United States Patent [19]

Rosevear

[11] 4,323,650

[45] Apr. 6, 1982

[54] IMMOBILIZATION OF BIOLOGICALLY ACTIVE SUBSTANCES IN A POROUS SUPPORT

[75] Inventor: Alan Rosevear, Faringdon, England

[73] Assignee: United Kingdom Atomic Energy Authority, London, England

[21] Appl. No.: 15,405

[22] Filed: Feb. 26, 1979

Related U.S. Application Data

[63] Continuation of Ser. No. 773,157, May 1, 1977, abandoned, which is a continuation of Ser. No. 587,201, Jun. 16, 1975, abandoned.

[30] Foreign Application Priority Data

Jun. 25, 1974 [GB] United Kingdom ............... 28212/74

[51] Int. Cl.³ .................... C12N 11/00; C12N 11/04; C12N 11/14
[52] U.S. Cl. .................................. 435/174; 435/176; 435/178; 435/182
[58] Field of Search ............... 435/174, 176, 177, 178, 435/174, 180, 181, 182

[56] References Cited

U.S. PATENT DOCUMENTS

| | | | |
|---|---|---|---|
| 3,705,084 | 12/1972 | Reynolds | 435/180 |
| 3,736,231 | 5/1973 | Stanley et al. | 435/177 |
| 3,804,719 | 4/1974 | Messing | 435/176 |
| 3,849,253 | 11/1974 | Harvey et al. | 435/182 |
| 3,850,751 | 11/1974 | Messing | 435/176 |

OTHER PUBLICATIONS

Olson et al., The Use of Tannic Acid and Phenol-Formaldehyde with Glutaraldehyde to Immobilize Enzymes, Proceedings of 166th National Meeting of the American Chemical Society, 1973, Immobilized Enzymes in Food and Microbiological Processes, Plenium Press, N.Y., 8/74, (pp. 54–61).

*Primary Examiner*—David M. Naff
*Attorney, Agent, or Firm*—Larson and Taylor

[57] ABSTRACT

Biologically active substances such as enzymes are immobilized in the pores of a porous support material by introducing a solution of the biologically active substance into the pores of the support material, treating the active substance in the pores to temporarily retain the active substance in the pores and immobilizing the active substance in the pores by crosslinking. Temporary retention of the active substance in the pores may be carried out by precipitation with a precipitating agent or by freeze-drying.

2 Claims, No Drawings

IMMOBILIZATION OF BIOLOGICALLY ACTIVE SUBSTANCES IN A POROUS SUPPORT

This application is a continuation of application Ser. No. 773,157, filed May 1, 1977, now abandoned, which is a continuation of application Ser. No. 587,201, filed June 16, 1975, now abandoned.

The present invention relates to the immobilization of biologically active substances, for example, enzymes, on a support material.

Biologically active substances, such as enzymes, are useful as catalysts in certain processes (e.g. amyloglucosidase in the production of glucose from starch). However, often in practice it is found that biologically active substances are available only in forms, such as enzyme preparations, which are water soluble. This means that such a substance cannot be economically isolated at the end of a process with the result that the substance is either lost in the spent liquor or contaminates the product.

Therefore it can be advantageous to immobilize a biologically active substance on a support material so that it can be separated from reaction media by physical techniques such as filtration or sedimentation. In addition biologically active substances immobilized on a support material are available for "localised" use, e.g. as a bed in a column.

A biologically active substance is considered to be immobilized on a support material if it is fixed thereon in such a manner that permits at least a major proportion of the substance to be retained by the support material under the particular process conditions in which the support material and biologically active substance are used.

Various methods for "fixing" or "immobilizing" (often referred to as "insolubilising") biologically active substances on support materials have previously been proposed in the art. However, these methods are unsatisfactory in that their products suffer from disadvantages. For example, the biologically active substance is either "leached" from the support material when in use and/or the physical, chemical or microbiological stability of the substance/support material combination is unsatisfactory with the result that the substance is not available for continued re-use over prolonged periods of time.

According to one aspect of the present invention there is provided a method for the preparation of a support material having immobilized thereon a biologically active substance comprising temporarily retaining a biologically active substance on a support material and treating the biologically active substance to cause cross-linking so as to immobilize biologically active substance on the support material.

The term "biologically active substance" as used in this specification embraces inter alia proteinaceous substances (e.g. enzymes), and includes substances which are biologically active per se and those which are not, but which can be activated after immobilization to make them biologically active.

Furthermore, it is to be understood that the term "biologically active substance" embraces inter alia those substances capable of participating in specific interactions, such substances including, for example, substances of biological origin and those which act on living organisms. Substances of synthetic origin which can participate in reactions involving specific interactions analogous to those which can occur with naturally occurring substances are also embraced within the term "biologically active substance".

In immobilising a biologically active substance in accordance with the present invention the substance is temporarily retained on the support material so that a substantial concentration of the substance is available to be immobilized on the support by cross-linking. Thus, the term "temporarily retaining" is not intended to relate particularly to the residence time of substance on the support, but to distinguish the nature of this retention step from the more permanent immobilization obtained by cross-linking.

Whilst adsorption of biologically active substance by the support material can occur during temporary retention, it has been found that the use of adsorption alone to effect temporary retention can give a low yield of immobilized enzyme. Thus, temporary retention in accordance with the method of the present invention very preferably involves treating the substance so as to form more than mere adsorptive retention by the support material.

The temporary retention of biologically active substance on the support material can be effected, for example, by precipitation from a solution of a biologically active substance by use of a precipitating agent. Alternatively, freeze-drying can be used in conjunction with a precipitating agent to effect temporary retention.

Freeze-drying alone can be used to effect temporary retention although it has been found that this can be less effective than when a precipitating agent is used.

Although a portion of a biologically active substance can be immobilized on the outer surface of a support material, in most circumstances it is very desirable to utilise the pores of a porous support material, since in this way, the surface area/volume ratio of the support material is greatly increased and thus a greater amount of biologically active substance immobilized. In these circumstances, the pore size and pore structure of the porous support material should be such as to permit entry of the substance to be immobilized and eventual entry of species with which the immobilized substance is to interact.

Thus, by using a porous support material and a biologically active substance which can enter the pores thereof, the method of the present invention enables biologically active substance to be immobilized in the pores of a porous support material. Thus, after temporary retention and cross-linking, biologically active substance immobilized on the porous support material will be present in the pores of the material as well as upon its outer surface. For example, in the case of a particulate porous support material a major proportion of the immobilized substance would be expected to be present in the pores rather than on the external surface thereof.

According to another aspect of the present invention there is provided a support material having immobilized thereon, by temporary retention and cross-linking, a biologically active substance.

In accordance with one particular embodiment of the invention the temporary retention is effected by precipitation and the precipitation and cross-linking processes are carried out sequentially by treating biologically active substance, previously introduced onto a porous support material, with a precipitating agent and then a cross-linking agent to cross-link the biologically active substance.

It has been found that it is possible to treat some biologically active substances with a precipitating and a cross-linking agent, or agents, simultaneously. This is possible in the case of enzymes (e.g. amyloglucosidase) where the time taken for cross-linking to occur far exceeds the time taken to precipitate the enzyme.

The temporary retention of some biologically active substances may be facilitated by pretreating the substance to cause a degree of cross-linking; in such cases a certain degree of cross-linking can precede precipitation.

Preferably a porous support material is first soaked in a concentrated solution of biologically active substance (e.g. an enzyme) and then is subsequently treated with a precipitating agent, which does not denature the substance, temporarily to retain biologically active substance on the porous support material and a cross-linking agent to cross-link and immobilize the substance on the porous support material.

In accordance with another particular embodiment of the invention a porous support material is soaked in a concentrated solution of biologically active substance (e.g. an enzyme), biologically active substance is temporarily retained on the porous support material by freeze-drying and the porous support material and temporarily retained biologically active substance are treated with a cross-linking agent, under conditions such that substantially no temporarily retained substance goes into solution, to effect cross-linking and immobilization of the substance on the support material.

Optionally, after temporarily retaining the substance on the porous support material by freeze-drying further biologically active substance can be introduced onto the porous support material, prior to cross-linking, by immersion in a concentrated solution of the substance and temporarily retained by treatment with a precipitating agent.

It will be appreciated that when carrying out the method of the present invention with a porous support material biologically active substance can be introduced, in solution, so as to fill the pore volume of the material and then treated, in such a way that significant amounts of the substance are not displaced from the pores, to cause the substance to come out of solution thereby to effect temporary retention of substance in the support material. The temporarily retained substance which is "localised" on the support material is subsequently cross-linked to immobilize it in the pores.

The immobilization of biologically active substances on a support material in accordance with the present invention involves sorption, entrapment and cross-linking.

Using the method of the present invention amyloglucosidase has been immobilized, using tannic acid as a precipitating agent and glutaraldehyde as a cross-linking agent, on the following inorganic materials which are given by way of example: porous titania spheroids, porous calcium phosphate spheroids, porous alumina spheroids, porous zirconia spheroids, controlled pore glass (Corning glass types CPG10-240; 10-370; 10-1250; 30-370 and 30-2000), crushed thermalite block, Laporte Spent Catalyst, Crosfield Spent Catalyst (Laporte and Crosfield Spent Catalysts contain porous alumino-silicate particles). It is to be understood that materials other than the foregoing examples are suitable for use as support materials. For example, porous natural earths such as Celite, are suitable support materials and enzymes have been immobilized in accordance with the present invention on porous spheroids fabricated from Celite. Furthermore, organic materials such as wood, Viscose, Sephadex (a cross-linked dextran), and Bio-gel (a polyacrylamide gel) can be used as support materials. For example, amyloglucosidase has been immobilized on wood chips using tannic acid as a precipitating agent and glutaraldehyde as a cross-linking agent. Very desirably the support material should be substantially insoluble under the process conditions and in the reaction media in which the support material and biologically active substance are used.

The following are examples of biologically active substances which have been immobilized on porous titania spheroids (having a particle size of 500$\mu$ diameter and 60% of the pores in the range 2700–10,000 Å diameter) using tannic acid as a precipitating agent and glutaraldehyde as a cross-linking agent: amyloglucosidase (four types), lactase (four types), $\alpha$-amylase, chymotrypsin, trysin, urease, glucose oxidase, lipoxidase, glucose isomerase and papain.

More than one biologically active substance can be immobilized on the same support in accordance with the present invention. Thus, amyloglucosidase and $\alpha$-amylase have been immobilized together.

A number of different reagents have been used as the precipitating agent in carrying out the method of the present invention. Thus, using glutaraldehyde as the cross-linking agent a commercially available amyloglucosidase (available under the name "Agidex") has been immobilized on porous titania spheroids (particle size and pore size as hereinbefore stated) using the following examples of precipitating agents: tannic acid in 70% ethanol, tannic acid in 50% acetone, tannic acid in 2:1 water/isopropanol, synthetic polyphenols in 50% acetone (available under the names Tannia, Fixoflex, Fixin, Hysolad from Harshaw Chemicals Ltd.), acetone, LT 24 Floccular (a flocculating agent available from Allied Colloids Ltd.), aqueous solutions of tannic acid, salmine sulphate, alginic acid, protamine sulphate, pectin, gallic acid, pyrogallol, polyethylene glycol, DEAE dextran, dextran sulphate, polygalacturonic acid and polyethyleneimine.

Amyloglucosidase (Agidex) has also been immobilized in accordance with the present invention on porous titania spheroids (particle and pore size as hereinbefore stated) using formaldehyde as the cross-linking agent and tannic acid as the precipitating agent and, additionally, using diethylpyrocarbonate as a cross-linking agent and each of the following examples of precipitating agents: aqueous tannic acid, salmine sulphate, alginic acid, protamine sulphate, pectin, and tannic acid in 70% ethanol. In addition, amyloglycosidase (Agidex) has been immobilized on porous titania spheroids (particle size and pore size as hereinbefore stated) using tannic acid as the precipitating agent and alkaline oxidation to cause cross-linking. Other cross-linking agents include glyoxal and bis-diazonium salts.

Also in accordance with the present invention glucose oxidase has been immobilized on titania spheroids using tannic acid and diethyl pyrocarbonate and papain has been immobilized on titania spheroids using tannic acid and formaldehyde.

The optimum conditions for immobilizing biologically active substances in accordance with the present invention are, at least in part, dependent upon the biochemical properties of the substance. Thus, the choice of, for example, precipitating agent, cross-linking agent and cross-linking time is optimised by experiment.

The time for immobilization can vary between say ½ hour to 24 hours depending on the biologically active substance.

The method of the present invention is preferably carried out at about 4° C. It has been noted that inactivation of certain biologically active substances can occur at higher temperatures. However, this depends on the substance and higher or lower temperatures could be appropriate.

It has been found that when immobilizing amyloglucosidase (Agidex) on porous titania spheroids (particle size and pore size as hereinbefore stated) by precipitation and cross-linking, the best performance from the point of view of enzyme activity of the immobilized enzyme is obtained by using tannic acid in acetone as the precipitating agent and glutaraldehyde as the cross-linking agent. For example, it has been found that using this particular combination of precipitating agent and cross-linking agent the apparent enzyme activity of amyloglucosidase (Agidex) immobilized on porous titania spheroids can be up to 20% of the enzyme activity of the aqueous enzyme preparation used as the source of amyloglucosidase.

Using 5% tannic acid in 5:1 acetone/water as a precipitating agent and gluteraldehyde as the cross-linking agent a batch of amyloglucosidase immobilized on porous titania spheroids (particle size and pore size as hereinbefore stated) was prepared from ~110 g titania spheroids and 30 ml Agidex, and packed into a column, 60 cm high and 100 mls in volume, to form a bed.

An acid thinned starch solution was passed through the column at a rate of between 52 and 230 ml/hr. The column was maintained at 60° for 8 days during which 9 liters of the solution were treated.

The Dextrose Equivalent (D.E.) of the product from the column was as high as that expected when a soluble enzyme is used for the same conversion process. The degree of hydrolysis of the product was constant during 7 days of steady use of the column.

A column of amyloglucosidase immobilized on porous titania spheroids was used continuously to hydrolyse a dextrin solution over a period of 7½ days. The product from the column had a constant D.E. value which indicated almost total conversion of the starting material. Subsequently, the column was washed free of dextrin solution, was stored for 5 weeks at room temperature and was re-used for the same hydrolysis process. The D.E. of the product was found to be the same as that obtained previously. The column was stored for a further 11 weeks and it was found that there was no serious loss in the enzyme activity.

It has been found that titania spheroids having amyloglucosidase immobilized thereon in accordance with the present invention may be used in either a packed bed, as described above, in a fluidised bed reactor or in a stirred tank reactor. It is to be expected that this will be so for many particulate support materials having biologically active substances immobilized on them in accordance with the present invention.

Amyloglucosidase has been immobilized on porous titania spheroids (particle size and pore size as hereinbefore stated) using freeze drying and a precipitating agent to effect temporary retention and glutaraldehyde to cause cross-linking.

Enzymes have been immobilized in situ on a column of porous titania spheroids.

During in situ immobilization excess biologically active substance not temporarily retained on the support material can be reclaimed for recycling by washing the support material (e.g. with acetone/tannic acid) prior to cross-linking.

Spent immobilized enzyme has been removed from titania spheroids and the spheroids re-used for further immobilization. Concentrated nitric acid, concentrated caustic soda or heating in a furnace were suitable for removing enzyme from the spheroids.

A wide range of biologically active substances can be immobilized on a wide range of support materials in accordance with the present invention. Consequently, the invention offers the advantage of flexibility over known "immobilization" methods in that a support material can be chosen from a wide range of materials, on the basis of its properties, to suit a particular application.

The present invention will now be illustrated by reference to the following examples.

EXAMPLE 1

Agidex solution (1 ml) was added to porous titania spheroids (3 ml; 500μ particle size and having 60% of the pores in the range 2700–10000 Å diameter), on an ice bath and was allowed to distribute throughout the spheroids. A 5% solution of tannic acid in 5:1 acetone:water (1.5 ml), previously cooled on an ice bath, was added followed by a 50% aqueous solution of glutaraldehyde (0.25 ml). The liquid level was then just above the surface of the porous titania spheroids. After 5 hours the spheroids were removed from the ice bath, washed and packed into a column so that the enzyme activity could be investigated. A solution of dextrin was used to investigate the properties of the column and, taking the activity of the original Agidex solution as 100%, the apparent activity of the immobilized enzyme in the column was found to be 20%.

EXAMPLE 2

Agidex solution (4.5 ml) was distributed throughout porous titania spheroids (15 ml) as in Example 1. A cooled 2% solution of tannic acid in acetone (6.75 ml), into which a 50% aqueous solution of glutaraldehyde (1.05 ml) had recently been mixed, was added and the resulting stiff slurry was thoroughly mixed. After 5 hours the spheroids were washed and the enzyme activity assayed as in Example 1. The apparent enzyme activity of the immobilized enzyme was found to be similar to that obtained in Example 1.

EXAMPLE 3

Agidex solution, diluted 1:1 with water (8 ml) was distributed throughout porous titania spheroids (10 ml; particle size and pore size as in Example 1) and was freeze-dried (lyophilised). Agidex solution (1.5 ml) was distributed throughout 5 ml of these lyophilised spheroids and a cooled 2% solution of tannic acid in acetone (2.25 ml) and 50% glutaraldehyde (0.35 ml) were added in the same way as Example 2. The apparent activity of the immobilized enzyme was found to be 15% more than the activity of immobilized enzyme prepared using porous titania spheroids, but no freeze-drying step.

EXAMPLE 4

Agidex solution (2 ml) was added to, and distributed throughout, 5 mls of porous glass particles (Corning CPG 10-1250, 36–75μ particle size) on an ice bath. A cooled 5% solution of tannic acid in 5:1 acetone:water (3 ml) was added followed by a 50% aqueous solution of glutaraldehyde (0.5 ml). After 5 hours the glass particles were washed and the enzyme activity investigated in a small stirred batch reactor. The apparent activity of the immobilized enzyme was 93% of the activity of enzyme immobilized on porous titania spheroids of the type used in Examples 1, 2 and 3.

EXAMPLE 5

Agidex solution (1 ml) was distributed throughout porous titania spheroids (3 ml) as in Example 1. 1.5 mls of a cooled 10% solution of Fixoflex (a synthetic polyphenol) in 5:1 acetone:water was added followed by a 50% aqueous solution of glutaraldehyde (0.25 ml). After 5 hours the spheroids were washed and when the immobilized enzyme was assayed as in Example 1 it was found to have 82% of the activity of immobilized enzyme prepared with tannic acid in an acetone:water mixture as the precipitating agent.

EXAMPLE 6

1 ml of an aqueous solution of lactase (Maxilact 75 mg/ml) was added to and distributed throughout 3 mls of porous titania spheroids. A cooled 0.25% solution of tannic acid in 5:1 acetone:water (1.5 ml) was added followed by a 20% aqueous solution of glutaraldehyde (0.1 ml). After 20 minutes the beads were washed and packed into a column. The apparent activity of the immobilized enzyme was 11% of the activity of the soluble enzyme when o-nitro phenyl-$\beta$-D galactoside was used as the substrate.

EXAMPLE 7

Agidex solution (1.5 ml) was added to porous titania spheroids (500$\mu$; 5 ml) on an ice bath and distributed throughout the spheroids. A cooled 2% solution of tannic acid in acetone (2.25 ml) was added followed by a 37% aqueous solution of formaldehyde (0.35 ml). After 5 hours the spheroids were washed and the immobilized enzyme was assayed as in Example 1. It was found to have an enzyme activity which was 56% of that of a similar immobilized enzyme prepared using glutaraldehyde as the cross-linking agent.

EXAMPLE 8

Agidex (1 ml) was distributed throughout a wad of soft wood chips, which occupied a volume of 3 mls, on an ice bath. A cooled 2% solution of tannic acid in acetone (1.5 ml) into which a 50% aqueous solution of glutaraldehyde (0.25 ml) had recently been mixed, was added and the reagents were thoroughly mixed. After 5 hours the chips were washed and loosely packed into a small column to enable the enzyme activity to be assayed as in Example 1. The chips had an enzymic activity which was 74% of the activity of the immobilized enzyme in Example 2.

EXAMPLE 9

An aqueous solution of glucose isomerase enzyme (1.5 ml obtained by aqueous extraction of Maxazyme-GI 14,000 cells) was allowed to soak into 5 g of porous titania spheroids (particle size of 500$\mu$ diameter and 60% of the pores in the range 2,200–10,000 Å diameter) on an ice bath.

The enzyme was precipitated and cross-linked by means of a solution of 3% tannic acid in acetone (2.25 ml) and 50% aqueous glutaraldehyde (0.05 ml).

After reacting for 1½ hours on an ice bath the spheroids were washed and the enzyme activity assayed.

It was found that the spheroids contained 35% of the enzyme activity present in the starting solution of the enzyme.

I claim:

1. A method for the preparation of a porous support material having a biologically active substance immobilised in the pores thereof comprising selecting a porous support material having a pore size and pore structure that permits entry of a solution containing biologically active substance, introducing said solution into the pores of said porous support material so as to substantially fill the pore volume of said support material, freeze-drying the volume of said solution introduced into the pores so as to retain said biologically active substance in the pores of the porous support material and hold the biologically active substance available for cross-linking, cross-linking the biologically active substance in the pores of the porous support material, said introduction of solution of containing biologically active substance and said freeze-drying being conducted so as to provide a major proportion of the immobilised biologically active substance in the pores of, rather than on the external surface of, the porous material.

2. A method as claimed in claim 1, wherein after the retention of the substance in the pores of the porous support material by freeze-drying, but prior to cross-linking, further biologically active substance is introduced into the porous support material by immersion in a concentrated solution of the substance, and is retained by treatment with a precipitating agent.

* * * * *